United States Patent [19]

Liu et al.

[11] Patent Number: 4,939,273

[45] Date of Patent: Jul. 3, 1990

[54] METHOD FOR CONVERSION OF ETHYLIDENE N,N'-BIS-PYRROLIDONE INTO 2-PYRROLIDONE

[75] Inventors: Kou-Chang Liu, Wayne; Paul D. Taylor, West Milford, both of N.J.

[73] Assignee: GAF Chemicals Corporation, Wayne, N.J.

[21] Appl. No.: 397,931

[22] Filed: Aug. 24, 1989

[51] Int. Cl.$^5$ ............................................. C07D 207/12
[52] U.S. Cl. .................................................. 548/543
[58] Field of Search ........................................ 548/543

[56] References Cited

U.S. PATENT DOCUMENTS 2,317,804  4/1943  Reppe et al. ........................ 548/543

Primary Examiner—Mary C. Lee
Assistant Examiner—Robert C. Whittenbaugh
Attorney, Agent, or Firm—Walter Katz; Marilyn J. Maue; Joshua J. Ward

[57] ABSTRACT

A method for conversion of ethylidene N,N'-bis-pyrrolidone, a by-product of the vinylation of 2-pyrrolidone, into 2-pyrrolidone starting material. This method is carried out by heating the by-product at an elevated temperature for a predetermined period of time, and recovering the 2-pyrrolidone conversion product therefrom for recycle into the vinylation process.

9 Claims, No Drawings

METHOD FOR CONVERSION OF ETHYLIDENE N,N'-BIS-PYRROLIDONE INTO 2-PYRROLIDONE

BACKGROUND OF THE INVENTION

1. Field of the Invention

This invention relates to production of vinyl pyrrolidone from 2-pyrrolidone and acetylene in the presence of a strongly basic catalyst, and more particularly, to a method of converting the ethylidene N,N'bis-pyrrolidone by-product of the reaction into 2-pyrrolidone starting material.

2. Description of the Prior Art

Reppe, in U.S. Pat. No. 2,317,804, described a process for preparing vinyl pyrrolidone by reaction of 2-pyrrolidone and acetylene in the presence of potassium hydroxide as a catalyst. The catalyst was prepared separately by reaction of potassium hydroxide with some of the 2-pyrrolidone starting material to produce the potassium salt of 2-pyrrolidone, which then acted as the desired strongly basic catalyst. This catalyst preparation stage then was followed by vinylation of the remainder of the 2-pyrrolidone starting material with acetylene in the presence of the potassium salt of 2-pyrrolidone catalyst.

A by-product of the vinylation reaction, however, has been identified as ethylidene N,N'-bis-pyrrolidinone (EBPY). However, this material was discarded during the process, thus reducing the yield of the desired vinyl pyrrolidone product.

Accordingly, it is the object of this invention to provide a method of converting EBPY into a compound useful in the process of vinylation of 2-pyrrolidone, thus increasing the effective yield of the vinyl pyrrolidone product.

SUMMARY OF THE INVENTION

What is described herein is a method of converting EBPY into 2-pyrrolidone, the starting material in the vinylation process. This method is carried out by heating EBPY at an elevated temperature for a predetermined period of time, and recovering the 2-pyrrolidone conversion product therefrom for recycle into the vinylation process.

DETAILED DESCRIPTION OF THE INVENTION

In accordance with the present invention, the process of vinylation of 2-pyrrolidone may be carried out in two stages. In the first stage, the strongly basic catalyst is prepared by reaction of 2-pyrrolidone starting material with potassium hydroxide to produce an active catalyst in the form of the potassium salt of 2-pyrrolidone. This reaction is carried out with removal of water to prevent formation of inactive potassium 4-aminobutyrate from the catalyst by ring opening of 2-pyrrolidone in the presence of water.

The second stage of the process involves reaction of 2-pyrrolidone and acetylene at about 25 to 125 psig acetylene partial pressure in the presence of the thus-prepared catalyst. The catalyst is employed in the process in a molar ratio of about 1:20 to about 1:200, preferably about 1:60 to 1:100, based on 2-pyrrolidone reactant.

If desired, a gas diluent can be employed with acetylene at a concentration of about 25 to about 200 wt. % of the total reaction mixture. The gas diluent, when used, may be selected from nitrogen, helium, argon, krypton, methane, ethane and propane, or mixtures thereof.

The reaction is generally effected at a temperature of about 125° C. to 185° C., for a period of about 2 to 20 hours, preferably at a temperature of about 135° C. to 165° C., for a period of about 5 to 15 hours. Under optimum conditions, the system is pressurized with about 70 to about 110 psig of acetylene and about 25 to 200 psig of gas diluent. More often, the gas diluent is employed at a partial pressure of about 60 to 125 psig.

The crude reaction product of the vinylation process is a mixture of the desired liquid vinyl pyrrolidone product, EBPY by-product and polymeric materials. The liquid vinyl pyrrolidone product can be easily separated from the non-volatile EBPY by-product and polymeric materials. The non-volatile residues then are subjected to the method of the invention, that is, to pyrolysis at an elevated temperature for a predetermined period of time. This treatment effectively converts EBPY to 2-pyrrolidone, which can be recycled into the system for use as starting material.

Generally, a pyrolysis temperature of about 120° to 300° C. is employed, preferably about 160° to 250° C., and the reaction is carried out for about 0.01 to 48 hours, preferably about 10 minutes to 1 hour. The percent conversion under these conditions is at least 10%, and usually about 40% to 95%, depending upon temperature and time of reaction.

A batch or continuous flow process may be used for this pyrolysis reaction, since the EBPY polymeric residue can flow through a hot tube at these temperatures. A reaction solvent is not needed; however, it can be used, if desired. Suitable reaction solvents include common organic liquids such as N-methylpyrrolidone, aromatic compounds and the like, which usually are used in an amount of about 30 to 70% by weight of the solution.

The invention now will be illustrated by reference to the following examples.

Example 1 below illustrates the pyrolysis reaction used to convert EBPY into 2-pyrrolidone.

EXAMPLE 1

Conversion of EBPY into 2-Pyrrolidone

A solution of 25 g. of ethylidene N,N'-bis-pyrrolidinone (EBPY) in 25 g. of N-methylpyrrolidinone solvent was charged into a 100 ml. round bottom flask. The solution then was heated at 150° C. and samples of the reaction product were withdrawn at various time intervals and analyzed by gas chromatography. The results are shown in the Table below.

TABLE

| Reaction Time, (hrs.) | Analysis of Reaction Product | | | |
|---|---|---|---|---|
| | EBPY (%) | 2-Pyrrolidone (%) | Conversion (%) | Yield (%) |
| 0 | 50.0 | 0.0 | — | — |
| 1 | 28.5 | 8.6 | 43.0 | 92.2 |
| 3 | 24.9 | 10.3 | 50.2 | 94.6 |
| 4 | 22.4 | 10.7 | 55.2 | 89.4 |
| 6 | 21.9 | 11.3 | 56.2 | 92.7 |
| 8 | 21.6 | 12.1 | 56.8 | 98.2 |
| 24 | 14.3 | 14.5 | 71.2 | 93.6 |

Example 2 below illustrates the continuous conversion of EBPY by-product into 2-pyrrolidone starting material for recycle into the vinylation process.

EXAMPLE 2

A. Vinylation Process

2-Pyrrolidone (628 g., 7.47 moles) was charged into a 1-liter, four-necked round bottom flask equipped with a condenser, mechanical stirrer, thermometer and nitrogen inlet, and heated to 80° C. Then potassium hydroxide (7.4 g., 85% pellet, 0.11 moles) was added. The solution was held at 90° C. and 0.1 mm Hg pressure for 1 hour to remove water from the solution. The treated solution then was transferred to a 1-liter stainless steel autoclave, purged three times with nitrogen at room temperature and then heated to 160° C. Then acetylene (partial pressure 100 psig) was added and the solution was agitated at a speed of 1800 rpm. After 8 hours of reaction, a 75% conversion of 2-pyrrolidone to N-vinyl pyrrolidone with 90% selectivity was obtained.

B. Conversion Process

The crude product from the vinylation process above was separated into distillable liquid materials and non-volatile residues. The non-volatile residues were passed through a hot tube maintained at 150° C. for a contact time of about 2 hours. The resultant product was exited from the heating zone and stripped of liquid material, which was mainly 2-pyrrolidone. The 2-pyrrolidone was recovered and recycled into the vinylation process.

Although the invention has been described with respect to certain embodiments thereof, it will be understood that changes and modifications may be made which are within the skill of the art. Accordingly, it is intended to be bound by the appended claims only.

What is claimed is:

1. A process for converting ethylidene-N,N'-bis-pyrrolidinone into 2-pyrrolidone which comprises pyrolyzing said ethylidene-N,N'-bis-pyrrolidinone at an elevated temperature.

2. A process according to claim 1 wherein said temperature is about 120° to 300° C.

3. A process according to claim 2 which is carried out for about 0.01 to 48 hours.

4. A process according to claim 3 in which at least a 10% conversion is obtained.

5. In a process of vinylation of 2-pyrrolidone with acetylene in the presence of a strongly basic catalyst, the step of converting the ethylidene-N,N'-bis-pyrrolidone by-product of said vinylation process into 2-pyrrolidone by pyrolysis of said ethylidene-N,N'-bis-pyrrolidone at about 120° to 300° C. for subsequent use as starting material in said process.

6. A process according to claim 5 wherein said pyrolysis is carried out in a batch process.

7. A process according to claim 5 wherein said step is carried out by continuously flowing said ethylidene-N,N'-bis-pyrrolidone through a hot tube.

8. A process according to claim 5 wherein said 2-pyrrolidone is recycled into the vinylation process.

9. A process according to claim 5 which is carried out for about 0.01 to 48 hours.

* * * * *